US009629786B2

(12) United States Patent
Mandeau et al.

(10) Patent No.: US 9,629,786 B2
(45) Date of Patent: Apr. 25, 2017

(54) MONOTERPENE DERIVATIVES OF CHALCONE OR DIHYDROCHALCONE AND THEIR USE AS DEPIGMENTING AGENTS

(75) Inventors: Anne Mandeau, Toulouse (FR); Stéphane Poigny, Saubens (FR); Françoise Belaubre, Villeneuve Tolosane (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 778 days.

(21) Appl. No.: 13/823,681

(22) PCT Filed: Jan. 18, 2012

(86) PCT No.: PCT/EP2012/050669
§ 371 (c)(1),
(2), (4) Date: Mar. 14, 2013

(87) PCT Pub. No.: WO2012/098134
PCT Pub. Date: Jul. 26, 2012

(65) Prior Publication Data
US 2013/0177515 A1 Jul. 11, 2013

(30) Foreign Application Priority Data

Jan. 18, 2011 (FR) .................... 11 50386

(51) Int. Cl.
| | |
|---|---|
| *A61Q 19/02* | (2006.01) |
| *A61Q 19/08* | (2006.01) |
| *A61K 36/28* | (2006.01) |
| *A61K 31/12* | (2006.01) |
| *A61K 8/35* | (2006.01) |
| *A61K 8/97* | (2006.01) |
| *A61K 36/54* | (2006.01) |
| *A61K 36/67* | (2006.01) |
| *C07C 49/835* | (2006.01) |

(52) U.S. Cl.
CPC .............. *A61K 8/35* (2013.01); *A61K 8/97* (2013.01); *A61K 31/12* (2013.01); *A61K 36/28* (2013.01); *A61K 36/54* (2013.01); *A61K 36/67* (2013.01); *A61Q 19/02* (2013.01); *A61Q 19/08* (2013.01); *C07C 49/835* (2013.01)

(58) Field of Classification Search
CPC ........ A61K 31/12; A61K 36/28; A61K 36/54; A61K 36/67; A61K 8/35; A61Q 19/02; C07C 49/835
See application file for complete search history.

(56) References Cited

U.S. PATENT DOCUMENTS

| | | | |
|---|---|---|---|
| 7,767,661 B2 | 8/2010 | Jia et al. | |
| 2006/0228313 A1 | 10/2006 | Perrier et al. | |
| 2009/0269419 A1 | 10/2009 | Pierrisnard et al. | |
| 2011/0159125 A1* | 6/2011 | Lyga ................. | A61K 8/44 424/757 |

OTHER PUBLICATIONS

JP 08-012522; English machine translation, Accessed May 28, 2015.*
Benosman et al., "New Terpenylated Dihydrochalcone Derivatives Isolated from Mitrella kentii", J. Nat. Prod., vol. 60 (1997) pp. 921-924.
Cavalli et al., "Constituents of the essential oil of six *Helichrysum* species from Madagascar", Flavour and Fragrance Journal, vol. 16 (2001) pp. 253-256.
Crombie et al., "Terpenylations Using (R)-(-)-α-Phellandrene. Synthesis of the (3S,4R)-8,9-Dihydro-o- and -p-cannabidiols, their iso-THC's, and the Natural Dihydrochalcone (3S,4R)-(+)-Linderatin", J. Chem. Soc. Perkin Trans., (1988) pp. 1251-1253.
Curto et al., "Inhibitors of Mammalian Melanocyte Tyrosinase: In Vitro Comparisons of Alkyl Esters of Gentisic Acid with Other Putative Inhibitors", Biochemical Pharmacology, vol. 57 (1999) pp. 663-672.
Ichino et al., "A New Flavanone, Neolinderatone, from Lindera Umbellata Thunb. Var. Lancea Momiyama", Chem. Pharm. Bull., vol. 37, No. 5, (1989) pp. 1426-1427.
Ichino et al., "Revised Structures of Linderatone and Methyllinderatone", Heterocycles, vol. 31, No. 3 (1990) pp. 549-553.
Ichino et al., "Studies on the Flavonoid Components of Lindera umbellata Thunb. var. membranacea (Maxim.) Momiyama", Chem. Pharm. Bull., vol. 37, No. 4 (1989) pp. 944-947.
Ichino et al., "Two Novel Flavonoids from the Leaves of Lindera Umbellata Var. Lancea and L. Umbellata", Tetrahedron, vol. 44, No. 11 (1988) pp. 3251-3260.
Ichino, "Two flavonoids from Two Lindera Umbellata Varieties", Phytochemistry, vol. 28, No. 3 (1989) pp. 955-956.
International Search Report issued in International Application No. PCT/EP2012/050669 on May 7, 2012.
Jimbow et al., "Intracellular Vesicular Trafficking of Tyrosinase Gene Family Protein in EU- and Pheomelanosome Biogenesis", Pigment Cell Res, vol. 13 (Suppl. 8) (2000) pp. 110-117.
Khatib et al., "Chalcones as potent tyrosinase inhibitors: the importance of a 2,4-substituted resorcinol moiety", Bioorganic & Medicinal Chemistry, vol. 13 (2005) pp. 433-441.
Kuwabara et al., "Topical Application of γ-Tocopherol Derivative Prevents UV-Induced Skin Pigmentation", Biol. Pharm. Bull., vol. 29, No. 6 (2006) pp. 1175-1179.
Mustafa et al., "Hydrogen-bonded rotamers of 2',4',6'-trihydroxy-3'-formyldihydrochalcone, an intermediate in the synthesis of a dihydrochalcone for Leptospermum recurvum", Tetrahedron, vol. 59 (2003) pp. 6113-6120.
Orjala et al., "New Monoterpene-Substituted Dihydrochalcones from Piper aduncum", Helvetica Chimica Acta, vol. 76 (1993) pp. 1484-1488.
Ortonne et al., "Latest Insights into Skin Hyperpigmentation", Journal of Invesigative Dermatology Symposium Proceedings, vol. 13 (2008) pp. 10-14.
Portet et al., "Activity-guided isolation of antiplasmodial dihydrochalcones and flavanones from Piper hostmannianum var. berbicense", Phytochemistry, vol. 68 (2007) pp. 1312-1320.
Thomson Scientific Database XP-002655240 of JP 8-012522A issued on Jan. 16, 1996.

* cited by examiner

*Primary Examiner* — Rachael E Bredefeld
(74) *Attorney, Agent, or Firm* — Birch, Stewart, Kolasch & Birch, LLP

(57) ABSTRACT

The present invention relates to new monoterpene derivatives of chalcone or dihydrochalcone and their use as a depigmenting agent.

7 Claims, No Drawings

MONOTERPENE DERIVATIVES OF CHALCONE OR DIHYDROCHALCONE AND THEIR USE AS DEPIGMENTING AGENTS

The present invention relates to the use in the field of depigmentation of monoterpene derivatives of chalcone or dihydrochalcone of the formula (I) and plant extracts containing them in cosmetic or dermatological compositions.

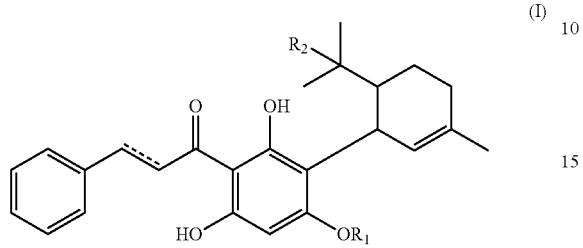

(I)

R1 = H, Me
R2 = H, OH

Trihydroxychalcones are disclosed for their depigmenting activity. The position of the OH groups is particularly important for this activity. 2',4',6'-Trihydroxychalcone (II) shows an IC50 on tyrosinase (monophenoloxidase activity on fungal tyrosinase) of 120 μM[i].

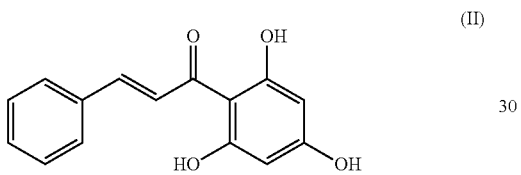

(II)

Surprisingly and unexpectedly, the inventors have shown that an additional substitution with a terpene or terpineol group (Formula I) greatly enhances this activity. This type of molecule is very seldom found in plants. To date, only three naturally existing compounds represented by the general formula (I) have been disclosed in literature: linderatin (III), linderachalcone (IV) and methyl-linderatin (V).

They have been isolated from:
Piper aduncum[ii], leaves, Piperaceae: (−)-methyl-linderatin,
Piper hostmannianum var. Berbicense[iii] leaves (Piperaceae): (+methyl-inderatin
Lindera umbellata var. membranacea[iv,v] and lancea[vi], leaves[vii] or barks[viii], Lauraceae: (+)-Linderatin, linderachalcone[ix], methyl-linderatin
Mitrella kentii, trunk bark, Annonaceae: (−)-Linderatin[x]

A compound with a closely related structure, gymnochalcone (VI), or alpha-terpineol pinocembrine chalcone, was first isolated by the inventors from aerial parts of Helichrysum gymnocephalum (DC) Humbert.

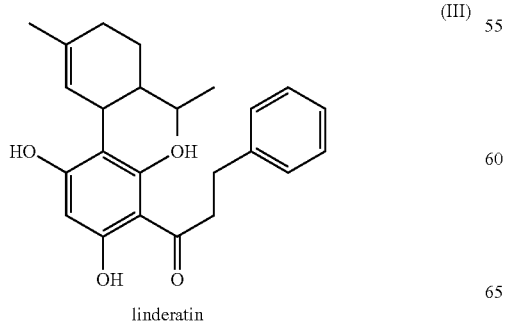

linderatin (III)

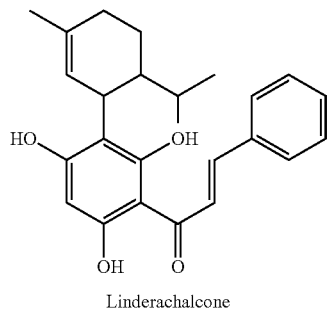

Linderachalcone (IV)

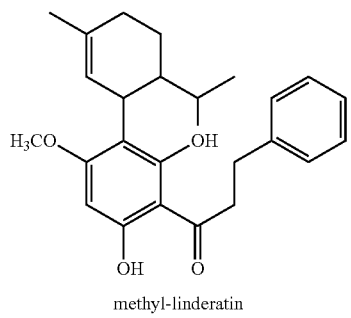

methyl-linderatin (V)

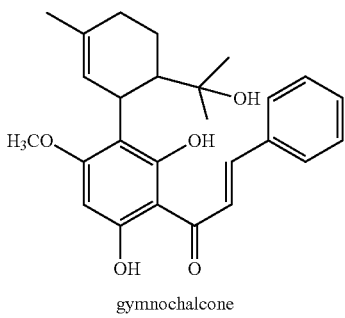

gymnochalcone (VI)

The inventors were also first to isolate linderatin from leaves of Piper aduncum.

With regard to the biological activities described, (−)-linderatin exhibited cytotoxicity on a cancer cell line (lung)[x], (−)-Methyl-linderatin has in turn an anti-plasmodial activity[iii].

None of the compounds above has been disclosed for their depigmenting activity.

A first object of the invention thus provides an extract of Helichrysum gymnocephalum (DC) Humbert enriched with one or more molecules of the following formula (I)

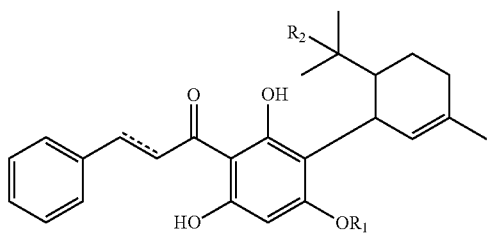

wherein
∥ is a single bond or a double bond;
R1=H or CH$_3$; and
R2H or OH
as a depigmenting agent.
It is preferred that R1=H.

Preferably, ∥ is a double bond, R1=H and R2=H or OH, or ∥ is a single bond, R1=H or CH$_3$ and R2=H.

More preferably, ∥ is a single bond, R1=H and R2=H, that is to say the extract according to the invention is enriched with linderatin.

More preferably, ∥ is a double bond, R1=H and R2=OH, that is to say the extract according to the invention is enriched with gymnochalcone. Such extract is particularly advantageous since surprisingly, the inventors have found that gymnochalcone is stable in time therein. In fact, cyclization of chalcones to flavanone, upon addition of a hydroxyl group on 1,4-position in the carbonyl group by a Michael type reaction, which brings about instability of the chalcones, is not observed in this case.
Such cyclization is observed for the purified gymnochalcone. Thus preferably gymnochalcone will be used in the form of an extract of *Helichrysum gymnocephalum*.

The inventors have shown that such extract of *Helichrysum gymnocephalum* of the invention is particularly advantageous for its depigmenting activity. The inventors have also shown that such activity is particularly specific of the species *Helichrysum gymnocephalum* since extracts prepared under the same conditions of *Helichrysum arenarium*, *Helichrysum cordifolium* and *Helichrysum stoechias*, although they all are rich in flavonoids and chalcones, do not exhibit any inhibiting activity for the synthesis of the melanin on B16 murine melanocytes.

Preferably, the extract according to the invention comprises one or more molecules of the formula I in an amount of between 0.1 and 30 g, preferably of between 0.1 and 10 g, most preferably of between 0.1 and 5 g, per 100 g of extract solids.

Advantageously, the extract according to the invention originates from aerial parts of *Helichrysum gymnocephalum* (DC) Humbert (Asteraceae, syn. *Stenocline gymnocephala*). It is prepared from this plant following traditional steps well known to those skilled in the art.

The aerial parts of *Helichrysum gymnocephalum* (DC) Humbert may be harvested at 5 different stages of growth of the plant: vegetative stage, pre-flowering stage, onset-of-flowering stage, flowering stage, fructification stage. Advantageously, the extract according to the invention originates from aerial parts of *Helichrysum gymnocephalum* (DC) Humbert at the fructification stage, preferably at the end of the fructification period.

The preferably dried plant is ground before being extracted with an organic solvent which may be an ester (ethyl acetate, isopropyl acetate), an alcohol (methanol, ethanol, propanol, isopropanol, butanol), a ketone (methyl ethyl ketone, dimethylketone, methyl isobutyl ketone), a halogenated hydrocarbon (chloroform, dichloromethane), water or a mixture of these solvents in any miscible proportion.

The extraction is performed at a plant/solvent ratio of between about 1/1 and about 1/20 and may be repeated 2 to 3 times. The temperature of the extraction solvent may range from room temperature to above ambient, up to the boiling temperature of the solvent involved. The contacting time of the plant with the solvent is from between about 30 min and about 72 hrs.

Then a solid/liquid separation is carried out, wherein the plant is separated from the solvent for example by filtration or centrifugation.

The filtrate obtained may be either:
directly taken to dryness by fully evaporating the solvent, to obtain the final extract, stored as a liquid in the extraction solvent if it is compatible with its intended use. In this case it may be more or less concentrated by an evaporation step, concentrated. This concentration step to a compound of interest may be carried out by techniques known to the one skilled in the art such as liquid/liquid extraction between 2 non miscible solvents, absorption onto a carrier such as silica, an ion-exchange resin, etc.

An extract obtained by extraction, solid/liquid separation followed by drying includes a mass amount of compound(s) comprised in the formula I of between 0.1 and 30 g, preferably between 0.1 and 10 g, most preferably between 0.1 and 5 g, per 100 g of extract dried material. If the extract is maintained in a solution, the dried material content of the liquid extract is between 0.1 and 80 g per 100 ml.

Another object of the invention relates to a process for preparing an extract according to the invention.

Another object of the invention relates to the cosmetic use of an extract of plant origin enriched with one or more molecules of the following formula (I) or the cosmetic use of a molecule of the following formula (I):

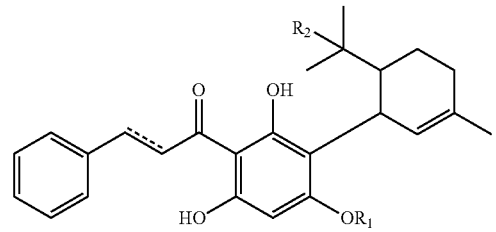

wherein
∥ is a single bond or a double bond;
R1=H or CH$_3$; and
R2=H or OH
as a depigmenting agent.

It is preferred that R1=H.

Preferably, ∥ is a double bond, R1=H and R2=H or OH, or ∥ is a single bond, R1=H or CH$_3$ and R2=H.

More preferably, ∥ is a double bond, R1=H and R2=OH, that is to say the invention relates to the cosmetic use of an extract of plant origin enriched with gymnochalcone; or to the cosmetic use of the gymnochalcone molecule.

More preferably, ∥ is a single bond, R1=H and R2=H, that is to say the invention relates to the cosmetic use of an extract of plant origin enriched with linderatin; or to the cosmetic use of the linderatin molecule.

Most preferably, the invention relates to the cosmetic use of an extract of plant origin comprising one or more molecules of the formula I in an amount of between 0.1 and 30 g, preferably between 0.1 and 10 g, most preferably between 0.1 and 5 g, per 100 g of extract dried material.

Said extract comprising one or more molecules of the formula (I) is preferably an extract of the invention or an extract of plants belonging to the genus *Helichrysum, Piper, Lindera* or *Mitrella*, including: *Piper hostmannianum, Piper hispidum, Piper aduncum, Lindera aggregata, Lindera umbellata, Lindera glauca, Mitrella mesnyi, Mitrella kentii*.

Most preferably, linderatin and methyl-linderatin will be used in cosmetics according to the invention in pure form, as synthetized, since they are stable in such form.

On the other hand, preferentially to the cosmetic use of pure gymnochalcone, the cosmetic use of an extract of *Helichrysum gymnocephalum* enriched with gymnochalcone will be favored since it is more stable therein than in the pure form.

Advantageously, the cosmetic use according to the invention is intended for bleaching and/or lightening the skin and/or bristles and/or hair, reducing and/or removing age spots from the skin or reducing and/or removing brownish pigment spots that can be induced by UV or chloasma.

The molecules of the formula (I) and/or the plant extracts containing them, as a depigmenting agent, have also shown good abilities to control and/or inhibit the production of melanins, which are responsible for pigmentation, thereby displaying an advantage in depigmentation of some unaesthetic pigment spots due to hyperpigmentation of the epiderm, especially age spots on skin.

The molecule of the formula (I) according to the present invention may be obtained by chemical or biochemical synthesis, or from a plant extract.

It is preferred that the molecule of the formula (I) is selected from the group consisting of:
gymnochalcone (Formula VI) wherein ∥ is a double bond, R1=H and R2=OH,
linderatin (Formula III) wherein ∥ is a single bond, R1=H and R2=H,
linderachalcone (Formula IV) wherein ∥ is a double bond, R1=H and R2=H,
methyllinderatin (Formula V) wherein ∥ is a single bond, R1=CH$_3$ and R2=H.

In the case where the molecule is gymnochalcone, the plant source will preferably be *Helichrysum gymnocephalum* (DC) Humbert; and more preferably the aerial parts of *Helichrysum gymnocephalum* (DC) Humbert, and even more preferably the aerial parts of *Helichrysum gymnocephalum* (DC) Humbert harvested at the fructification stage.

In the case where the molecule is linderatin, it will preferably be obtained by chemical synthesis.

In the case where the molecule is a linderatin of plant origin, the plant source will preferably be *Lindera umbellata* var. *membranacea* and *lancea*; and more preferably the leaves or barks thereof.

Another object of the invention relates to a cosmetic or dermatological composition comprising, as an active ingredient, an extract of plant origin enriched with one or more molecules of the following formula (I), or one or more molecules of the following formula (I):

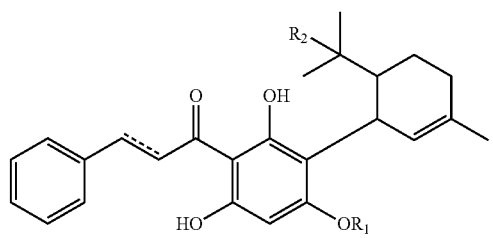

wherein
∥ is a single bond or a double bond;
R1=H or CH$_3$; and
R2=H or OH.

It is preferred that R1=H. Preferably, ∥ is a double bond R1=H and R2=H or OH, or ∥ is a single bond, R1=H or CH$_3$ and R2=H.

More preferably, ∥ is a double bond R1=H and R2=OH, that is to say the invention relates to a cosmetic or dermatological composition comprising, as an active ingredient: a plant extract enriched with gymnochalcone, or the gymnochalcone molecule.

More preferably, ∥ is a single bond, R1=H and R2=H, that is to say the invention relates to a cosmetic or dermatological composition comprising, as an active ingredient: a plant extract enriched with linderatin; or the linderatin molecule.

Most preferably, the invention relates to the cosmetic or dermatological composition of the invention which comprises, as an active ingredient, an extract of plant origin comprising one or more molecules of the formula I in an amount of between 0.1 and 30 g, preferably between 0.1 and 10 g, most preferably between 0.1 and 5 g, per 100 g of extract dried material.

Advantageously, said extract is an extract of the invention or an extract of plants belonging to the genus *Helichrysum, Piper, Lindera* or *Mitrella*, including: *Piper hostmannianum, Piper hispidum, Piper aduncum, Lindera aggregata, Lindera umbellata, Lindera glauca, Mitrella mesnyi. Mitrella kentii.*

Another object of the invention relates to a dermatological composition according to the invention for use as a medicament.

Another object of the invention relates to a dermatological composition according to the invention for use for depigmenting the skin and/or bristles and/or hair.

Another object of the invention relates to a dermatological composition according to the invention for use in the treatment of hyperpigmentation of the skin.

Advantageously, the cosmetic composition according to the invention is used for reducing and/or removing and/or preventing pigmentation spots on the skin.

Advantageously, the cosmetic composition according to the invention is used for bleaching and/or lightening the skin and/or bristles and/or hair.

The use of a molecule of the formula I and/or a plant extract containing such molecule according to the present invention thus makes it possible to even out the skin tone: which is characterized by a uniform, lighter, more transparent, brighter skin tone. This results in the brightness of the skin tone being therefore improved.

Advantageously, the cosmetic composition according to the invention is used for evening out the skin tone.

The advantages obtained with the composition according to the present invention are particularly beneficial to sensitive skins, regardless of their nature (dry, normal, oily), and more particularly for sensitive skins which are dull and lack brightness.

Advantageously, the cosmetic composition according to the invention is used in sensitive skins.

The use of the molecules of the formula (I) and/or the plant extracts containing them according to the present invention is advantageous for:
either reducing and/or removing spots of pigmentation, such as spots of hyperpigmentation due to proinflammatory stress, for example UV-induced brownish pigment spots, or reducing and/or removing chloasma;
reducing and/or inhibiting the production of melanins, which are responsible for pigmentation.

The cosmetic and/or dermatological compositions according to the invention may include, besides the active ingredient(s), a physiologically acceptable medium; i.e. which is compatible with the skin and/or the scalp, the mucous membranes, the hair, the bristles and/or the eyes.

Preferably, the cosmetic or dermatological composition according to the present invention comprises an amount of the molecule of the formula (I), as an active ingredient, of between 10 mg and 5 g, and more preferably between 100 mg and 1 g per 100 g of said composition.

Preferably, the cosmetic or dermatological composition according to the present invention comprises an amount of the plant extract of the invention, as an active ingredient, of between 0.1 g and 10 g, and more preferably between 1 g and 5 g per 100 g of said composition.

The cosmetic and/or dermatological composition according to the present invention may advantageously be provided in any dosage forms usually used in the cosmetic and dermatological fields for topical or oral use.

Preferably, the topical form may be particularly provided in the form of:

an optionally gelled aqueous or hydroalcoholic solution, an optionally two-phase lotion-type dispersion, an oil-in-water or water-in-oil or multiple emulsion, an aqueous gel, and may be provided as a serum, a cream, a gel, an ointment, a milk, a lotion, a paste or a foam. It may also be applied as an aerosol or as a solid, including for example in the form of a stick.

One of the advantages of the present invention is that the compositions according to the invention show a good skin tolerance, even on sensitive skins, regardless of their nature (dry, normal, oily).

This composition may also be provided in an oral dosage form, such as a tablet, a capsule, a powder for drinkable suspensions.

The composition may also comprise any components usually used for the intended application. Those include water, solvents, mineral, animal and/or vegetable oils, waxes, pigments, chemical or mineral filters, antioxidants, fillers, surfactants, stabilizers, preservatives, aromas, and coloring agents.

The composition may also combine a depigmenting active ingredient according to the invention with other depigmenting actives well known to those skilled in the art, including: vitamin C derivatives, resorcinol derivatives more particularly 4-n-butylresorcinol or 4-(1-phenylethyl)benzene-1,3-diol, hydroquinone, arbutin, kojic acid and derivatives thereof, tocopherol derivatives.

The choice and/or the amount of the one or more ingredients will be also determined by the specific needs of the skin and/or bristles and/or hair to which the composition will be applied, as well as by the properties and consistency that are desired for the composition according to the present invention.

Another object of the invention relates to a cosmetic method for bleaching and/or lightening the skin and/or bristles and/or hair comprising the application to the skin and/or bristles and/or hair of a cosmetic composition according to the invention.

Another object of the invention relates to a cosmetic method for reducing and/or removing and/or preventing pigmentation spots on the skin comprising the application on the skin of a cosmetic composition as defined in the invention.

Another object of the invention relates to a molecule of the following formula (VI)

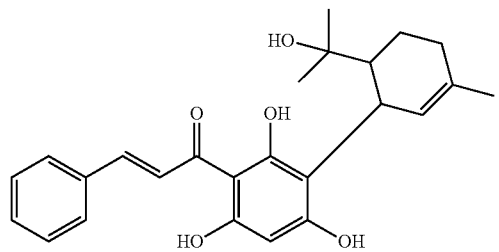 [SMILES: CC1=CC(c2c(O)cc(O)c(C(=O)/C=C/c3ccccc3)c2O)C(C(C)(C)O)CC1]

It is preferably obtained by chemical or biochemical synthesis, or from a plant extract.

The invention will be better understood with reference to the following non-limiting examples which are specific embodiments of the cosmetic and/or dermatological compositions according to the invention.

EXAMPLE 1

Preparation of an Extract of Aerial Parts of *Helichrysum gymnocephalum*

5 kg of dried aerial parts were extracted twice with 35 and 25 L of 95% ethanol under reflux. The combined filtrates were concentrated and dried. The extract obtained, in the form of a brown paste, contained 0.28 g of gymnochalcone per 100 g of solids.

EXAMPLE 2

Preparation of Linderatin by Chemical Synthesis

The linderatin was obtained by a two-step synthesis following the reaction scheme below, disclosed in literature[xv,xvi]

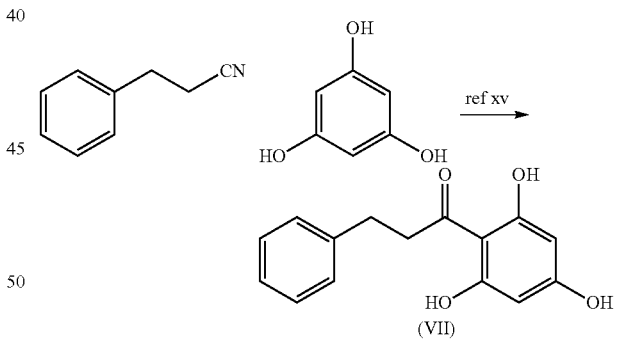

The synthesis of molecule (VII) was performed by condensation of phloroglucinol (2,4,6-trihydroxybenzene) with hydrocinnamonitrile in the presence of $ZnCl_2$ and HCl gas in anhydrous ether.

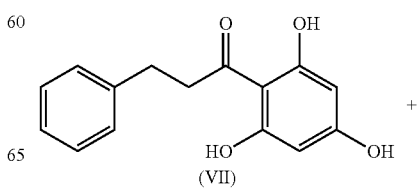

-continued

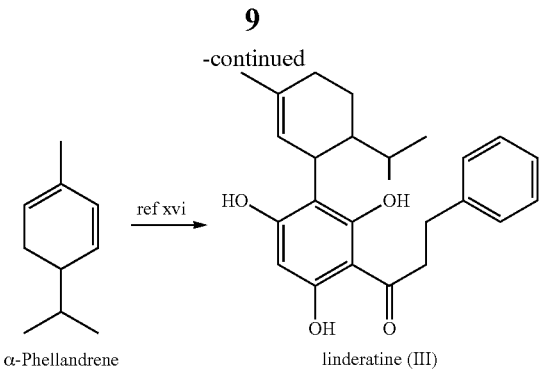

α-Phellandrene          linderatine (III)

Linderatin was then obtained by condensation of α-phellandrene which is commercially available from Sigma Aldrich (95%) and the molecule (VII) in the presence of para-toluene sulfonic acid in anhydrous benzene.

The resulting linderatin was identical in all respects to the natural product disclosed in literature[xvi].

EXAMPLE 3

Preparation of Gymnochalcone from the Aerial Parts of *Helichrysum gymnocephalum*

The aerial parts were dried and ground, before being extracted with ethyl acetate. Such extract was fractionated on a medium pressure silica column eluted with heptane, dichloromethane and acetone, resulting in 11 fractions after TLC analysis and combination of identical fractions. Active fraction 8 was then fractionated on C-18 grafted silica with a gradient of acetonitrile/water+0.1% acetic acid, resulting in isolation of gymnochalcone of the formula VI (0.02% yield/dry plant).

Structural Data:

Analysis by electrospray source mass spectrometry in positive ion mode gave the adduct $[M+Na]^+=431.3$ and $[2M+Na]^+=839.4$. In negative ion mode, $[M-H]^-=407.3$ was found. The mass of the compound was therefore 408 g/mol. In MS/MS a 152 fragment was released corresponding to α-terpineol (or p-menth-1-en-8-ol).

Mono- and bi-dimensional proton and carbon NMR analysis resulted in the identification of the structure in relative configuration, having the empirical formula $C_{25}H_{28}O_5$.

(VI)

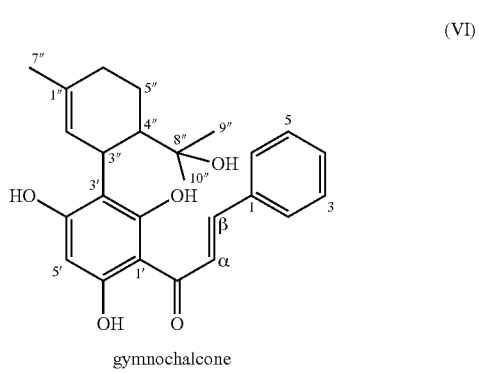 [SMILES: CC1=CC(c2c(O)cc(O)c(C(=O)/C=C/c3ccccc3)c2O)C(C(C)(C)O)CC1]

gymnochalcone

The NMR profile was characteristic of 2',4',6'-trihydroxychalcone (II), except in the 3' position. It was also very close to that of linderachalcone (IV)[ix], with the exception of the 8", 9" and 10" positions, which were further deshielded due to the presence of a hydroxyl function at 8".

TABLE 1

NMR shifts (in ppm) of the proton and carbon atoms of gymnochalcone in deuterated chloroform.

| Position | Functional group | 1H | 13C |
|---|---|---|---|
| 1 | CIV | / | 137.2 |
| 2 | CH | 7.62 | 129.3 |
| 3 | CH | 7.62 | 129.3 |
| 4 | CH | 7.4 | 129.4 |
| 5 | CH | 7.4 | 129.9 |
| 6 | CH | 7.4 | 129.9 |
| α | CH | 8.22 | 130.9 |
| β | CH | 7.72 | 142.4 |
| C=O | CIV | / | 194.16 |
| 1' | CIV | / | 105 |
| 2' | CIV | / | 167 |
| 3' | CIV | / | 112.9 |
| 4' | CIV | / | 164 |
| 5' | CH | 5.95 | 93.9 |
| 6' | CIV | / | 161.6 |
| 1" | CIV | / | 133.7 |
| 2" | CH | 5 | 126.8 |
| 3" | CH | 3.8 | 34.9 |
| 4" | CH | 2.5 | 46.9 |
| 5" | CH2 | 1.41 | 26.5 |
| 6" | CH2 | 1.94 | 31.5 |
| 7" | CH3 | 1.65 | 23.5 |
| 8" | CIV | / | 74.77 |
| 9" | CH3 | 1 | 29.4 |
| 10" | CH3 | 1.13 | 25.4 |

EXAMPLE 4

Preparation of Methyl-Linderatin from Leaves of *Piper Aduncum*

The leaves were dried and ground, before being extracted with ethanol 96 (1 wt/10 vol) by maceration at room temperature for 15 hrs, in the dark. This extract (17% yield) was fractionated on a medium pressure silica column eluted with heptane, ethyl acetate and methanol, resulting in 21 fractions after TLC analysis and combination of identical fractions. Fractions 3 and 4 were subsequently fractionated by semi-preparative HPLC on C-18 grafted silica with a gradient of acetonitrile/water, resulting in isolation of methyllinderatin of the formula V (13% yield/extract, 2.2%/dry plant).

The NMR and mass spectrometry data were consistent with those disclosed in literature for methyllinderatin[ii].

EXAMPLES OF COSMETIC COMPOSITIONS

Example 1

Depigmenting Serum

| Compound | Amounts |
|---|---|
| Linderatin | 0.1 g |
| (Di)Sodium EDTA | 0.05 to 0.5 g |
| Cetearyl alcohol/Ceteareth 33 | 1 to 10 g |
| Caprylyl (Di)Ether | 1 to 10 g |
| Glyceryl stearate | 1 to 8 g |
| (Cyclopenta)decamethyl Siloxane | 1 to 10 g |
| Capric caprylic/trigly. 30 70 | 1 to 10 g |
| Glycolic acid | 1 to 5 g |
| Sodium hydroxide | 1 to 3 g |
| Benzoic acid | qs |
| Purified water | to 100 g |

Example 2

Bleaching Cream

| Compound | Amounts |
| --- | --- |
| Dry extract of *Helichrysum gymnocephalum* | 0.5 g |
| Carbomer K | 0.2 to 2 g |
| Purified Chlorphenesine | 0.05 to 1 g |
| Phenoxyethanol | qs |
| Cetyl alcohol | 0.1 to 2 g |
| Sorbitan palmitate | 1 to 8 g |
| (Poly) Sorbate 40 | 0.1 to 2 g |
| Capric caprylic/trigly. 30 70 | 1 to 10 g |
| (p)Ethylhexyl methoxycinnamate | 1 to 10 g |
| (alpha) Tocopheryl acetate | 0.5 g |
| (Tri)Ethanolamine | 0.8 g |
| MBBT/Decylglucoside Mix | 1 to 10 g |
| Purified water | to 100 g |

Pharmacological Testing: Inhibition of Melanin Synthesis:

Melanocytes are star-shaped cells, which are contained in minor proportion in the basal layer of the epidermis. Their main function is to insure melanogenesis, a process whereby melanin is synthetized to specialized organelles, known as melanosomes, then transported and distributed to the neighboring keratinocytes via their dendritic extensions. This contact with keratinocytes enables skin pigmentation, a protection mechanism of the epidermis against the mutagenic effects of ultraviolet rays. Each melanocyte is related with about thirty-six keratinocytes, thus forming an <<epidermal-melanin unit>>.

Melanogenesis consists of a series of enzymatic and spontaneous reactions, having tyrosine as a precursor. Three major enzymes take part in this process: tyrosinase, and tyrosinase-related proteins 1 and 2 (TRP 1 and 2)[xi].

Some exogenous molecules are known to down-regulate melanogenesis. Hydroquinone inhibits melanin synthesis by providing a substrate for tyrosinase in order to divert its activity[xii]. Arbutin which contains hydroquinone acts in the same way. Kojic acid decreases the activity of tyrosinase by inhibiting UV-induced hyperpigmentation[xiii]. Vitamin C inhibits tyrosinase but also behaves like a powerful reducer by preventing oxidative coloration of melanin. Vitamin A decreases the expression of tyrosinase and TRP-2[xiv].

We have developed a test for measuring melanin synthesis by using a colorimetric assay on the murine melanoma cell line B16-F10. This assay enables to test the depigmenting power of active ingredients.

| Compound | IC50 |
| --- | --- |
| Gymnochalcone | 17 µM |
| Linderatin | 5 µM |
| Methyllinderatin | 6 µM |
| Kojic acid | 2400 µM |
| Arbutin | 158 µM |
| Hydroquinone monomethyl ether | 31 µM |
| EtOH95 extract of *Helichrysum gymnocephalum* | 10 µg/ml |

[i] Bioorganic & Medicinal Chemistry 13, 2005, 433-441
[ii] Orjala J. et al. New monoterpene-substituted dihydrochalcones from *Piper aduncum*. *Helv. Chem. Acta* 1993, 76, 1481-1488
[iii] Portet B. et al., Activity-guided isolation of antiplasmodial dihydrochalcones and flavanones from *Piper hostmannianum* var. *berbicense*. *Phytochemistry* 2007, 68, 1312-1320
[iv] Ichino K. et al., Revised structures of Linderatone and methyllinderatone. *Heterocycles* 1990, 31, 549-553.
[v] Ichino K. et al., Studies on the flavonoid components of *Lindera umbellata* THUNB. Var. *membranacea* (MAXIM.) MOMIYAMA *Chem Pharm Bull* 1989 37, 944-947
[vi] Ichino K. et al., A new flavanone, neolinderatone, from *Lindera umbellata* THUNB. Var. *Lancea* MOMIYAMA. *Chem Pharm Bull* 1989, 37, 1426-1427
[vii] Ichino K. et al., Two novel flavonoids from the leaves of *Lindera umbellata* var. *Lancea* and *L. umbellata*. *Tetrahedron* 1988, 44, 3251-3260
[viii] Shimomura H. et al., A chalcone derivative from the bark of *Lindera umbellata*. *Phytochemistry* 1988, 27, 3937-3939
[ix] Ichino K., Two flavonoids from two *Lindera umbellata* varieties. *Phytochemistry* 1989, 28, 955-956
[x] Benosman A. et al., New terpenylated dihydrochalcone derivatives isolated from *Mitrella kentii*. J. Nat. Prod. 1997, 60, 921-924.
[xi] Jimbow, K. et al. Intracellular vesicular trafficking of tyrosinase gene family protein in eu- and pheomelanosome biogenesis. *Pigment Cell Res.* 2000; 13 Suppl 8.:110.-7.13 Suppl 8, 110-117.
[xii] Curto, E. V. et al. Inhibitors of mammalian melanocyte tyrosinase: in vitro comparisons of alkyl esters of gentisic acid with other putative inhibitors. *Biochem. Pharmacol.* 1999, 57, 663-672.
[xiii] Kuwabara, Y. et al. Topical Application of gamma-Tocopherol Derivative Prevents UV-Induced Skin Pigmentation. *Biol. Pharm. Bull.* 2006. June; 29. (6.):1175.-9.29, 1175-1179
[xiv] Ortonne, J. P. and Bissett, D. L. (2008) *J. Investig. Dermatol. Symp. Proc.* 2008. April; 13(1):10-4.13, 10-14
[xv] Kamarul, A. M et al. *Tetrahedron* 59 (2003), 6113
[xvi] Crombie L, et al. *J. Chem. Soc. Perkin Trans*. 1988, 1251

The invention claimed is:

1. A method for bleaching and/or lightening one or more selected from skin, bristles and hair of a subject, which comprises:
   administering to said one or more selected from skin, bristles and hair a cosmetic composition comprising:
   a compound of formula (I)

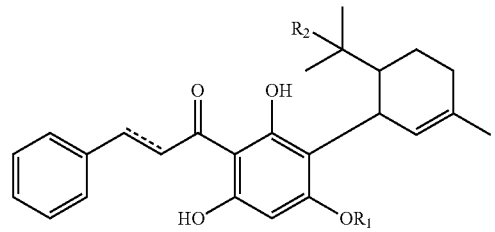

wherein:
   ⫶ is a double bond,
   $R_1$=H or $CH_3$, and
   $R_2$=OH.

2. The method of claim 1, wherein the cosmetic composition further comprises an extract, wherein the extract is an extract of plants selected from the genus of *Helichrysum, Piper, Lindera* and *Mitrella*.

3. The method of claim 2, wherein the plants are selected from *Helichrysum gymnocepahlum* (DC) Humbert, *Piper hostmannianum, Piper hispidum, Piper aduncum, Lindera aggregata, Lindera glauca, Lindera umbellatta, Mitrella mesnyi* and *Mitrella kentii*.

4. A method for reducing, removing and/or preventing pigmentation spots on the skin of a subject, which comprises:
   administering to the skin of the subject a cosmetic composition comprising:
   a compound of formula (I)

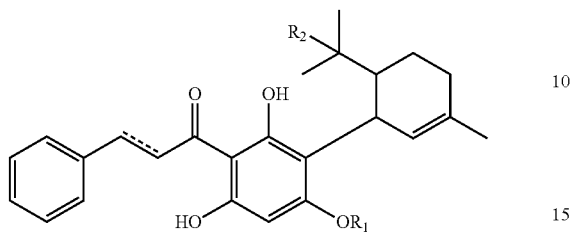

wherein:
∥ is a double bond,
R1=H or CH$_3$, and
R2=OH.

5. The method of claim 4, wherein the pigmentation spots are induced by UV light or cholasma, or are age spots.

6. The method of claim 4, wherein the cosmetic composition further comprises an extract, wherein the extract is an extract of plants selected from the genus of *Helichrysum, Piper, Lindera* and *Mitrella*.

7. The method of claim 6, wherein the plants are selected from *Helichrysum gymnocepahlum* (DC) Humbert, *Piper hostmannianum, Piper hispidum, Piper aduncum, Lindera aggregata, Lindera glauca, Lindera umbellatta, Mitrella mesnyi* and *Mitrella kentii*.

* * * * *